(12) United States Patent
Zhang et al.

(10) Patent No.: US 7,429,691 B2
(45) Date of Patent: Sep. 30, 2008

(54) METHODS AND COMPOSITIONS FOR TRANSFORMATION AND REGENERATION OF MAIZE

(75) Inventors: Shibo Zhang, Albany, CA (US); Rosalind Carrier, Springfield, OR (US); Peggy G. Lemaux, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 108 days.

(21) Appl. No.: 10/526,663

(22) PCT Filed: Sep. 3, 2003

(86) PCT No.: PCT/US03/27565

§ 371 (c)(1), (2), (4) Date: Jan. 19, 2006

(87) PCT Pub. No.: WO2004/022707

PCT Pub. Date: Mar. 18, 2004

(65) Prior Publication Data

US 2006/0174367 A1    Aug. 3, 2006

Related U.S. Application Data

(60) Provisional application No. 60/408,142, filed on Sep. 3, 2002.

(51) Int. Cl.
    *C12N 15/82*    (2006.01)
(52) U.S. Cl. .................. 800/278; 435/424; 435/430
(58) Field of Classification Search .................. None
    See application file for complete search history.

(56) References Cited

U.S. PATENT DOCUMENTS

| | | |
|---|---|---|
| 4,003,156 A | 1/1977 | Sibi et al. |
| 4,699,644 A | 10/1987 | Brandt et al. |
| 5,164,310 A | 11/1992 | Smith et al. |
| 5,281,529 A | 1/1994 | Zhong et al. |
| 5,320,961 A | 6/1994 | Zhong et al. |
| 5,350,688 A | 9/1994 | Matsuno et al. |
| 5,403,736 A | 4/1995 | Tanimoto |
| 5,405,765 A | 4/1995 | Vasil et al. |
| 5,480,789 A | 1/1996 | Firoozabady et al. |
| 5,565,355 A | 10/1996 | Smith |
| 5,589,617 A | 12/1996 | Nehra et al. |
| 5,610,042 A | 3/1997 | Chang et al. |
| 5,639,949 A | 6/1997 | Ligon et al. |
| 5,641,664 A | 6/1997 | D'Halluin et al. |
| 5,736,369 A | 4/1998 | Bowen et al. |
| 5,948,956 A | 9/1999 | Lee et al. |
| 6,140,555 A | 10/2000 | Reichert et al. |
| 6,162,900 A | 12/2000 | Guerinot et al. |
| 6,235,529 B1 | 5/2001 | Lemaux et al. |
| 6,486,384 B1 * | 11/2002 | Zhang et al. .................. 800/293 |
| 6,541,257 B2 | 4/2003 | Lemaux et al. |

FOREIGN PATENT DOCUMENTS

| | | |
|---|---|---|
| EP | 0558676 | 9/1993 |
| JP | 01027466 | 1/1989 |
| JP | 07213183 | 8/1995 |
| JP | 07255304 | 10/1995 |
| WO | WO-92/20809 | 11/1992 |
| WO | WO-94/13822 | 6/1994 |
| WO | WO-96/04392 | 2/1996 |
| WO | WO-97/17429 | 5/1997 |

OTHER PUBLICATIONS

Zhang S. et al. Production of multiple shoots from shoot apical meristems of oat (Avena sativa L.) J. Plant Physiology, 1996, 148: 667-671.*
Zhong H. et al. In-vitro morphogenesis of corn (Zea mays L.), 1992, Planta, 187:483-489.*
Dodds J.H. et al. Experiments in Plant Tissue Culture, 2nd edition, Cambridge University Press 1985, pp. 210-211.*
Abbas, M. A. et al. (1993) "Growth and Some Metabolic Activities of Maize Plants in Response to Copper Pollution," *Journal of Environmental Sciences* 6:145-158.
Doncheva, S. et al. (1996) "Effect of Copper Excess on the Morphology of the Nucleus in Maize Root Meristem Cells," *Physiologia Plantarum* 96:118-122
Doncheva, Snejana (1997) "Ultrastructural Localization of Ag-NOR Proteins in Root Meristem Cells After Copper Treatment," *J. Plant Physiol.* 151:242-245.
Zhang, S. et al. (1999) "Genetic Transformation of Commercial Cultivars of Oat (*Avena sativa L.*) and Barley (*Hordeum vulgare L.*) Using in Vitro Shoot Meristematic Cultures Derived from Germinated Seedlings," Plant Cell Reports 18:959-966.
Zhang, S. et al. (2002) "Transformation of Recalcitrant Maize Elite Imbreds Using in Vitro Shoot Meristematic Cultures Induced from Germinated Seedlings," *Plant. Cell Rep.* 21:263-270.
Int'l Search report, dated May 17, 2004, Int'l Appln. No. PCT/US2003/027565.
Ali, Gayoor et al. (1999) "Morphogenic and Biochemical Responses of Bacopa Monniera Cultrues to Zinc Toxicity," Plant Science, 143: 187-193.
Baillie et al., 1992, "Field evaluation of barley (*Hordeum vulgare* L.) genotypes derived from tissue culture," Can. J. Plant. Sci., 72:725-733.
Bhaskaran et al., 1990, "Regeneration in Cereal Tissue Culture: A Review," Crop Sci., 30:1328-1337.
Bhojwani, S. S. et al. (1983) Chapter 3 In Plant Tissue Culture: Theory and Practice, Elsevier, Amsterdam, pp. 25-41.

(Continued)

*Primary Examiner*—Cynthia Collins
(74) *Attorney, Agent, or Firm*—Morrison & Foerster LLP

(57) ABSTRACT

Methods for transforming plants, particularly commercially important elite maize inbreds, are provided. The methods involve transformation of meristematic organogenic tissue or immature embryos, and include the use of defined plant growth media. The methods disclosed provide more stable transgenic plants, and permit the transformation of varieties of cereals that are not amenable to transformation by conventional approaches.

7 Claims, 5 Drawing Sheets

OTHER PUBLICATIONS

Bregitzer et al, 1995, "Plant regeneration from Barley Callus: Effects of 2, 4-dichlorophenoxyacetic acid and phynylacetic acid," Plant Cell Tiss. Org. Cult., 43:229-235.

Bregitzer et al. (1998) "Enhancement of Plant Regeneration from Embryogenic Callus of Commercial Barley Cultivars," Plant Cell Reports 17(12): 941-945.

Bergitzer, 1992, "Plant Regeneration and Callus Type in Barley: Effects of Genotype and Culture Medium," Crop Sci., 32:1108-1112.

Casas et al. (1997) "Transgenic Sorghum Plants Obtained after Mircoprojectile Bombardment of Immature Inflorescences," In Vitro Cell. Dev. Biol.—Plant 33: 92-100.

Christensen et al., 1996, "Ubiquitin promoter-based vectors for high-level expression of selectable and/or screenable marker genes in monocotyledonous plants," Trangenic Res., 5:1-6.

Dahleen, 1995, "Improved plant regeneration from barley callus cultures by increased copper levels," Plant Cell Tiss. Org. Cult., 43:267-269.

Dahleen, Lynn S. (Jul. 1996) Public message posted on Plant-tc Bulletin Board located at <http://plant-tc.coafes.umn.edu/listserv/1996/log9607/msg00093.html>.

De Block et al., 1987, "Engineering herbicide resistance in plants by expression of a detoxifying enzyme," EMBO J., 6:2513-2518.

Fletcher, (1969) "Retardation of Leaf Senescence by Benzy-ladenine in Intact Bean Plants," Planta, 89:1-8.

Fromm et al., (1986) "Stable transformation of maize after gene transfer by electroporation," Nature, 319:791-793.

Fromm et al., (1989) "An Octopine Synthase Enhancer Element Directs Tissue-Specific Expression and Binds ASF-1, a Factor from Tobacco Nuclear Extracts," Plant Cell, 1:977-984.

Funatsuki et al., (1995) "Fertile transgenic barley generated by direct DNA transfer to protoplasts," Theor. Appl. Genet., 91:707-712.

Ghaemi et al., (1994) "The effects of silver nitrate, colchicines, cupric sulfate and genotype on the production of embryoids from anthers of tetraploid wheat (*Triticum turgidum*)," Plant Cell Tiss. Org. Cult., 36:355-359.

Gless et al. (1988), "Transgenic Oat Plants Obtained at High Efficiency by Microprojectile Bombardment of Leaf Base Segments," J. Plant Physiol., 152:151-157.

Goldstein et al., (1986) "Tissue culture and plant regeneration from immature embryo explants of Barley, *Hordeum vulgare*, " Theor, Appl. Genet., 71:631-636.

Gordon-Kamm et al., (1990) "Transformation of Maize Cells and Regeneration of Fertile Transgenic Plants," Plant Cell, 2:603-618.

Griffin et al., (1995) "High-frequency plant regeneration from seed-derived callus cultures of Kentucky bluegrass (*Pao pratensis* L.)," Plant Cell Rep., 14:721-724.

Hagio et al., (1995) "Production of fertile trangenic barley (*Hordeum vulgare* L.) plant using the hygromycin-resis-tance marker," Plant Cell Rep., 14:329-334.

Hanzel et al., (1985) "Genotype and Media Effects on Callus Formation and Regeneration in Barley," Crop Sci., 25:27-31.

Holm et al., (1994) "Regeneration of fertile barley plants from mechanically isolated protoplasts of the fertilized egg cell," Plant Cell, 6:531-543.

Holtorf et al., (1995) "Two routes of chlorophyllide synthesis that are differentially regulated by light in barley (*Hordeum vulgare* L.)," Proc. Natl. Acad. Sci. USA, 92:3254-3258.

Hossain, B. et al. (1997) "Internal Zinc Accumulation is Correlated with Increased Growth in Rice Suspension Culture," J Plant Growth Regul, 16: 239-243.

Jahne et al., (1991) "Regeneration of fertile plants from protoplasts derived from embryogenic cell suspensions of barley (*Hordeum vulgare* L.)," Plant Cell Rep., 10:1-6.

Jahne et al., (1994) "Regeneration of trangenic, microspore-derived, fertile barley," Theor. Appl. Genet., 89:525-533.

Jahne, A. et al. (1991) "Plant Regeneration from Embryonic Cell Suspensions Derived from Anther Cultures of Barley (*Hordeum Vulgare* L.)," Theor Appl. Genet, 82: 74-80.

Jain et al., (1995), "An improved procedure for plant regeneration from indica and japonica rice protoplasts," Plant Cell Reports, 14:515-519.

Kasha et al., (1991) "Haploids in Cereal Improvement: Anther and Microspore Cultures," In: Gene Manipulation in Plant Improvement II, Gustafson (ed.), Plenum Press: New York, pp. 213-235.

Kott et al., (1984) "Initiation and morphological development of somatic embryoids from barley cell cultures," Can. J. Bot., 62:1245-1249.

Lemaux et al., (1996) "Bombardment-Mediated Transformation Methods for Barley," Bio-Rad US/EG Bulletin 2007: 1-6.

Luhrs et al., (1987) "Plant regeneration in vitro from embryo-genic cultures of spring- and winter-type barley (*Hordeum vulgare* L.) varieties," Theor. Appl. Genet., 75:16-25.

Luthra, Rajesh et al. (1997) "Microprojectile Mediated Plant Transformation: A Bibliographic Search," Euphytica 95: 269-294.

Murakami et al., (1986) "The bialaphos Biosynthetic genes of *Streptomyces hygroscopicus*: Molecular cloning and char-acterization of the gene cluster," Mol. Gen. Genet., 205:42-50.

Napoli et al. (1990), "Introduction of a Chimeric Chalcone Synthase Gene into Petunia Results in Reversible Co-Suppression of Homlogous Genes in trans," The Plant Cell, 2:279-289.

Ortiz, Pablo A. et al. (1996) "Hygromycin Resistance as an Efficient Selectable Marker for Wheat Stable Transformation," Plant Cell Reports 15: 877-881.

Pasternak, Taras P. et al. (1999) "Embryogenic Callus Formation and Plant Regeneration from Leaf Base Segments of Barley (*Hordeum vulgare* L.)," J. Plant Physiol, 155: 371-375.

Potrykus (1991), "Gene Transfer to Plants: Assessment of Published Approaches and Results," Annu. Rev. Plant Physiol. Plant Mol. Biol., 42:205-225.

Purnhauser (1991) "Stimulation of Shoot and Root Regeneration in Wheat Triticum Aestivum Callus Cultures by Copper," Cereal Research Communications, 19: 419-424.

Salmenkallio-Marttila et al., (1995) "Transgenic barley (*Hor-deum vulgare* L) by electroporation of protoplasts," Plant Cell Rep., 15:301-304.

Somers et al. (1992), "Fertile, Transgenic Oat Plants," Biotechnology, 10:1589-1594.

Thompson et al., (1987) "Characterization of the herbicide-resistance gene bar from *Streptomyces hygroscopicus*," EMBO J., 6:2519-2523.

Torbet et al. (1995), "Use of paromomycin as a selective agent for oat tranformation," Plant Cell Reports, 14:635-640.

Vain et al. (1993) "Osmotic Treatment Enhances Particle Bombardment-Mediated Transient and Stable Transformation of Maize," Plant Cell Reports, 12: 84-88.

Wan et al. (1995), "Type I callus as a bombardment target for generating fertile transgenic maize (*Zea mays* L.)," Planta, 196:7-14.

Wan et al., (1994) "Biolistic Transformation of Microspore-13 Derived and Immature Zygotic Embryos and Regenerations of Fertile Transgenic Barley Plants," In: Gene Transfer to Plants, eds. Potrykus and Spangenberg, Springer Verlag, pp. 139-146.

Wan, Yuechun et al. (1994) "Generation of Large Numbers of Independently Transformed Fertile Barley Plants," Plant Physiology, 104: 37-48.

Zaghmout et al. (1992), "Plant Regeneration from Callus and Protoplasts of Perennial Ryegrass (*Lolium perenne* L.)," J. Plant Physiol., 140:101-105.

Zhang et al., (1996) "Production of Multiple Shoots Apical Meristems of Oat (*Avena sativa* L.)," J. Plant Physiol, 148:667-671.

Zhang, S. et al. (1998) "Expression of CDC2Zm and KNOTTED1 During In-Vitro Axillary Shoot Meristem Proliferation and Adventitious Shoot Meristem Formation in Maize (*Zea mays* L.) and Barley (*Hordeum vulgare* L.)," Planta. 204: 542-549.

Zhong et al. (1996), "The Competence of Maize Shoot Meristems for Integrative Transformation and Inherited Expression of Transgenes," Plant Physiol., 110:1097-1107.

Zhong et al., (1991) "Plant regeneration via somatic embryo-genesis in creeping bentgrass (*Agrostis palustris* Huds.)," Plant Cell Rep., 10:453-456.

Zhong et al., (1992) "In-vitro morphogenesis of corn (*Zea mays* L.)," Planta, 187:483-489.

\* cited by examiner

METHODS AND COMPOSITIONS FOR TRANSFORMATION AND REGENERATION OF MAIZE

RELATED APPLICATIONS

This application is a U.S. national phase application of International Application No. PCT/US2003/027565, filed Sep. 3, 2003, which claims priority to Provisional Application Ser. No. 60/408,142 filed Sep. 3, 2002, all of which are hereby incorporated by reference in their entirety.

FIELD OF THE INVENTION

This invention relates to compositions and methods for the in vitro culture, transformation, and regeneration of maize.

BACKGROUND OF THE INVENTION

The ability to genetically engineer monocots, including cereal crops, to improve their performance and pest-resistance, or to enhance alternative uses is of great importance. Genetic improvement of various crop species by genetic engineering has sometimes been hindered because techniques for in vitro culture, transformation, and regeneration of amenable cultivars are less effective with recalcitrant commercial cultivars.

In particular, the development of stable transformation technologies for cereal plants is largely dependent on the availability of efficient methods for inducing and maintaining large numbers of undifferentiated plant cells in culture.

Virtually all current genetic engineering technologies require that genes be delivered to cells grown in vitro. Many published methods for generating fertile transformed plants from cereals (e.g. rice, wheat, maize, oat, sorghum, triticale, barley and rye) utilize as initial explants the immature scutellum of the embryo or microspores directly or tissue derived from immature embryos or microspores. From these initial explants, cellular proliferation occurs. Maintenance and regeneration of these proliferating cells is required for almost all stages of genetic transformation methods. The cells can then be stably transformed with the gene or genes of interest and the transformed cells can be selected. After selection or screening for transformants, plants are regenerated.

Most transformation protocols require that the target tissue undergo embryogenesis, which may include de-differentiation of a single original transformed cell before the sustained cell divisions that give rise to an embryo consisting mostly or entirely of cells that contain the introduced DNA. De-differentiation during in vitro culturing introduces stresses on the genome, causing modifications of the genome that are associated with somaclonal variation, including DNA methylation, point mutations, deletions, insertions, and the generation of gross cytogenetic abnormalities. These genomic modifications lead to subsequent phenotypic abnormalities and performance losses and may contribute to other problems Transformation methods using excised shoot apices have been previously described (see, for example, U.S. Pat. No. 5,164,310 to Smith et al.; Zhong et al. 1996, both of which are herein incorporated by reference). However, these methods have not proven to be effective for maize that include commercially important elite inbreds. There is a need, therefore, for improved methods for plant transformation and regeneration, particularly for use with maize elite inbreds.

SUMMARY OF THE INVENTION

The invention provides methods and compositions for plant cell culture, transformation and regeneration that are applicable to maize, including commercially important elite maize inbreds that have proven difficult or impossible to transform and regenerate by previously available methods. Such maize lines include B73, Ohio 43, Missouri 17, PHJ90, PHR81, PHP02, PHN46, and PHP38, PHTE4 and PHJ90. These improved methods result in significantly higher regeneration frequencies, reduced somaclonal variation, improved transgene expression stability, and reduced albinism.

In the methods of the invention, seeds and immature ears may be utilized as starting material. For seeds, the seeds are sterilized and then germinated on germination medium. Vegetative shoot segments including the shoot apical meristem and stem tissues are isolated from 7-10 day old germinated seedlings. The vegetative shoot segments are then cultured on meristem proliferation media either containing elevated zinc levels or not.

For immature ears, the immature ears are sterilized and then dissected to isolate immature embryos. These immature embryos are placed on germination medium to produce vegetative shoot segments. The vegetative shoot segments are then cultured on meristem proliferation media either containing elevated zinc levels or not.

One transformation method disclosed relies on introducing the nucleic acid sequence (generally referred to as the "transgene") into shoot meristematic tissue that is typically derived from axillary shoot meristem, stem tissue, or a leaf base. This tissue requires little or no de-differentiation in order to regenerate plants that express the transgene. Thus, in contrast to embryogenic callus tissue (a conventional target for transformation), these meristematic tissues do not undergo significant de-differentiation in the transformation process. Rather, these cells require only a simple redirection of growth in order to produce whole transgenic plants. The present invention also provides plant growth media containing growth substrates (including suitable levels of plant hormones and other components) with which the efficient production and regeneration of this meristematic tissue can be achieved. In particular, the invention provides media suitable for the production of meristematic tissue that is highly amenable to transformation from cultivars of monocots that are otherwise recalcitrant to transformation.

The meristematic tissue is incubated In the light on a meristem proliferation medium (MPM) to induce production of adventitious meristematic cells, which are then used as the target for nucleic acid transformation. Alternatively, plant tissue can be transformed first and then subsequently used to produce transformed adventitious meristematic cells. Transformation may be achieved by any effective means, including for example conventional particle bombardment. MPM promotes fast growth of meristematic cells without promoting shoot or root formation. Particular compositions of MPM that are provided by this invention include components such as maltose, copper and zinc that are important to the success of the transformation methods; these compositions are designated MPM-MC and MPM-Zn. MPM-MC typically comprises plant auxin and cytokinin hormones, usually in a low auxin/high cytokinin ratio. Thus, MPM-MC typically includes from 0 mg/L to about 3 mg/L of an auxin and from about 1 mg/L to about 10 mg/L of a cytokinin. MPM-MC also includes an elevated level of copper, generally from about 0.1 $\mu$M to about 50 $\mu$M, and typically within the range of about 1 to about 10 $\mu$M. In addition, maltose is generally used as a carbon/sugar source in MPM-MC medium, typically at a concentration of from about 20 g/L to about 60 g/L, and usually at about 30 g/L. Other carbon sources, such as sucrose, may be used in place of, or in combination with, maltose. In addition, MPM-Zn has elevated zinc levels. In standard MS-based media, the concentration of $Zn^{2+}$ is 30 µM. The new media, MPM-Zn, is based on the discovery that, for certain maize genotypes, the induction of shoot meristematic cultures (SMCs) is improved, when elevated levels of $Zn^{2+}$ are present in the culture medium. The $Zn^{2+}$ concentration of MPM-Zn is usually greater than about 30 µM and may be greater than about 35 µM. Generally, the $Zn^{2+}$ concentration of MPM-Zn falls within the range of about 60 µM to about 1500 µM and is typically between about 100 µM and about 500 µM.

Following introduction of the nucleic acid into adventitious meristematic tissues, the meristematic tissues are typically transferred to fresh MPM-MC or MPM-Zn, or other suitable media, and incubated in the light. Thereafter, a selection agent may be introduced to the culture medium in order to select for transformed meristematic cells and meristematic structures. Transformed cells and structures are identified by their enhanced growth on this selection medium compared to untransformed material, and are subsequently removed and transferred to a regeneration medium for rooting.

The invention also provides methods for obtaining multiple transformed plants following the transformation of immature embryos. Such methods involve introducing a nucleic acid into an immature embryo, allowing the transformed tissue to proliferate, selecting transformed shoots from transformed embryos, inducing the transformed shoots from transformed embryos to produce SMCs comprised of transformed adventitious meristematic cells essentially as described above, regenerating transformed shoots from transformed meristematic cells, and rooting the transformed shoots.

These and other aspects of the invention will become more apparent from the following detailed description.

DETAILED DESCRIPTION OF THE INVENTION

Figure 1:
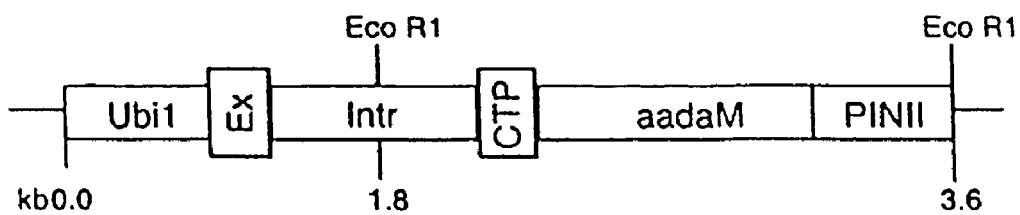
FIG. 1A-C shows schematic diagrams of DNA constructs used in maize inbred transformation. (A) p11593 containing a modified streptomycin-resistance gene (aadaM) driven by the maize ubi1 promoter (Ubi1) plus exon1 (Ex), intron1 (Intr), and CTP box (CTP), terminated with Pin2 terminator (Pin2). (B) p8092K containing a maize optimized PAT gene (MO-PAT) driven by the maize ubi1 promoter (Ubi1) plus intron1 (Intr), terminated with CaMV 35S terminator (35S). (C) pAGR73 containing uidA (uidA) driven by the rice act1 promoter (Act1 5') plus exon1 (Ex) and intron1 (Intr), terminated with rbcS terminator (rbcS 3'). Sizes of plasmids are noted in parentheses; EcoRI and BamHI sites are as indicated.
Figure 1:
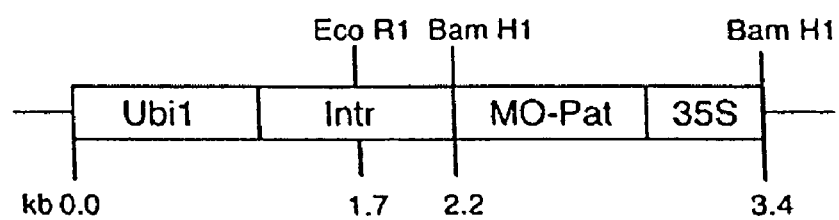
Figure 1:
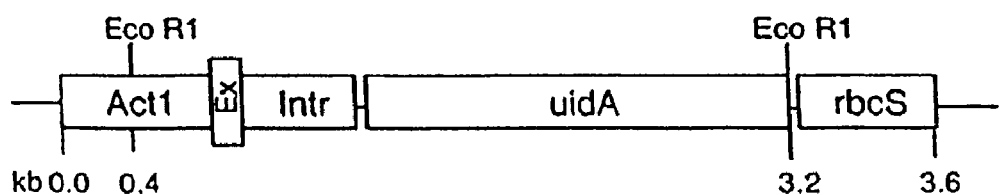

The invention also provides methods for obtaining multiple transformed plants following the transformation of immature embryos. Such methods involve introducing a nucleic acid into an immature embryo, allowing the transformed tissue to proliferate, selecting transformed shoots from transformed embryos, inducing the transformed shoots from transformed embryos to produce SMCs comprised of transformed adventitious meristematic cells essentially as described above, regenerating transformed shoots from transformed meristematic cells, and rooting the transformed shoots.

The disclosed methods are particularly useful for transformation of commercial inbred lines of maize (B73, Ohio 43, Missouri 17, PHTE4, PHJ90, PHR81, PHP02, and PHP38) that are recalcitrant to transformation using published embryogenic callus approaches.

Plant Culture Media and Methods

Unless otherwise noted, terms are to be understood according to conventional usage by those of ordinary skill in the relevant art. In addition to the definitions of terms provided below, definitions of common terms in molecular biology may also be found in Rieger et al., 1991; and Lewin, 1994.

The plant culture media of the invention may contain phytohormones. Phytohormones are also known in the art as plant growth regulators, plant hormones, or simply, hormones. Phytohormones of the invention include, but are not limited to, both free and conjugated forms of naturally occurring plant growth regulators. Additionally, the plant growth regulators of the invention encompass synthetic analogues, inhibitors of the synthesis, degradation, transport or action, and precursors of such naturally occurring plant growth regulators. Preferred plant growth regulators include auxins, cytokinins, abscisic acid and ethylene, and conjugates, synthetic analogues, inhibitors and precursors thereof.

Naturally occurring and synthetic analogues of auxins include, but are not limited to, 2,4-dichlorophenoxyacetic acid (2,4-D), dicamba, indoleacetic acid (IAA), 3-indolebutyric acid (IBA), α-napthaleneacetic acid (NAA), 4-(2,4-dichlorophenoxy) butyric acid, 2,4,5-trichlorophenoxyacetic acid (2,4,5-T), (4-chloro-2-methylphenoxy)acetic acid (MCPA), 4-(4-chloro-2-methylphenoxy) butanoic acid (MCPB), mecoprop, dicloprop, quinclorac, picloram, triclopyr, clopyralid, fluroxypyr and dicamba.

Naturally occurring and synthetic analogues of cytokinins include, but are not limited to, kinetin, zeatin, zeatin riboside, zeatin riboside phosphate, dihydrozeatin, $N^6$-(2-isopentenyl) adenine (2iP), 6-benzylaminopurine (BAP) and thidiazuron (TDZ), zeatin riboside phosphate, dihydrozeatin, isopentyl adenine and 6-benzyladenine.

It is recognized that the methods of the invention can involve plant culture media that do not contain any phytohormones. Such plant culture media are referred to as phytohormone-free, or hormone-free, plant culture media.

a. In vitro Culture of Transformed Meristematic Plant Cells

Meristematic tissue is comprised of minimally differentiated plant cells that are capable of repeated division to yield other meristematic cells as well as more differentiated cells that elongate and further specialize to form structural tissues and organs of the plant. Meristematic tissue for use in the transformation methods described herein may be obtained from axillary shoots, stem tissues, as well as leaf bases.

The media used for in vitro culture of meristematic tissue to produce adventitious meristems and to regenerate transformed meristematic tissue contribute significantly to the successful production of fertile transgenic plants. In addition, selection of the fastest-growing tissue improves the long-term regenerability of the cultures.

b. Meristem Proliferation Medium (MPM)

Meristematic tissue within a plant organ (e.g., vegetative shoots) is cultured on MPM medium, which promotes a fast growth rate and proliferation of meristematic cells without promoting shoot and root formation. In addition, following DNA introduction into meristematic tissue, the transformed tissues may or may not be incubated on MPM for a time sufficient for individual transformed cells to proliferate, thereby ensuring that a sufficient number of progeny cells are produced from each transformation event to increase the likelihood that the initial transformation event leads to the regeneration of a plant containing transformed tissue.

MPM preferably has a low auxin/high cytokinin ratio. Auxin levels in MPM are typically about 0 mg/L (no auxin) to about 3.0 mg/L For maize, for example, the preferred levels are about 0 mg/L to about 0.5 mg/L. Cytokinin levels in MPM are typically about 1 mg/L to about 10 mg/L, about 2 mg/L to about 4 mg/L are preferred. Cytokinins may improve regenerability and reduce the incidence of albinism. The optimal level of cytokinin (and particularly the optimal ratio of auxin to cytokinin) depends on the genotype and the species being transformed.

Any auxin or cytokinin may be used in MPM, regeneration medium (RM) or any other plant culture medium of the invention. Auxins and cytokinins include, but are not limited to, those described supra. The cytokinins BAP and 2iP are typically employed in culture media used for maize transformation. Those of ordinary skill in the art recognize, however, that a particular genotype or species may respond optimally to specific phytohormones.

MPM-Zn\ refers to the particular formulation of MPM used-in certain aspects of the invention. MPM-MC is formulated with hormones as described above, and is supplemented with maltose and copper. MCM-MC contains copper generally at a concentration of at least 0.1 μM (the level in typical plant growth media, such as MS medium), and more typically at least 10-100 fold higher, i.e. from about 1 to about 10 μM.

In certain formulations, MPM-MC contains even higher levels of copper, for example up to about 50 μM. Optimal copper and maltose levels vary with the genotype and species. The term "copper" is intended to include any well-known nutritional source of copper for plant culture media, e.g., cupric sulfate. Generally, the preferred concentrations of maltose and copper in MPM-MC are those that allow the formation and/or proliferation of adventitious meristematic tissues. MPM-Zn is identical to MPM-MC respectively, described supra, except for higher levels of $Zn^{2+}$ (zinc). In standard MS-based media, the concentration of $Zn^{2+}$ is 30 μM. The new media, MPM-Zn, is based on the discovery that, for certain cereal genotypes, the induction of shoot meristematic cultures (SMCs) is improved, when elevated levels of $Zn^{2+}$ are present in the culture medium. The $Zn^{2+}$ concentration of MPM-Zn is usually greater than about 30 μM. Generally, the $Zn^{2+}$ concentration of MPM-Zn and falls within the range of about 60 μM to about 1500 μM and is typically between about 100 μM and about 500 μM.

In addition, MPM also includes a sugar/carbon source, generally at about 20 g/L to about 60 g/L, with about 30 g/L being typical. In MPM-MC, maltose is the preferred carbon/sugar source, particularly for recalcitrant maize genotypes, although sucrose or other conventional carbon sources for plant tissue culture can also be used. While MPM will generally contain a sugar/carbon source at about 20 g/L to about 60 g/L, it is recognized that concentrations higher than 60 g/L can also be employed in the media of the invention. In MPM, concentrations of sugar, particularly maltose, can be up to about 150 g/L or even about 200 g/L.

Maltose and elevated copper levels were tested separately and in combination in various formulations of MPM to observe their effects on in vitro culture of adventitious meristems. In some maize genotypes, the combination of maltose and elevated copper levels was critical for the successful induction and long-term proliferation of shoot meristematic tissue.

As discussed in the Examples below, optionally MPM can be supplemented with a conventional osmoticum for a short time (e.g., about 4 hours) prior to (and optionally, after for a short period, e.g. 18 h) microprojectile bombardment. For example, the MPM can be supplemented with equimolar mannitol and sorbitol to give a final concentration of 0.4 M. Similarly, MPM can also be supplemented with high concentrations of maltose, generally about 100 g/L to about 150 g/L. However, good results have also been obtained when such an osmoticum was not included in MPM prior to (or after) bombardment.

As noted above, the methods and media described herein can be used to produce and maintain adventitious meristematic tissue for long periods of time. To maintain adventitious meristematic tissue, it is generally divided into smaller pieces (e.g., pieces of about 3 to 5 mm) and subcultured, i.e., transferred to fresh medium, at regular intervals (e.g. 2 weeks) to promote optimal growth rates.

If a selectable marker is used to identify transformed tissues, the meristematic tissues may be initially cultured after transformation without selection in order to allow for the proliferation of transformed cells in the absence of dead or dying cells resulting from the selection agent. The optimal period for proliferation without selection varies with the species. After this period, selection can be applied to select for transformed cells. Selection can be accomplished by adding a selection agent to the culture medium for which the foreign DNA in transformed cells confers resistance (assuming that a selectable marker is included on the foreign DNA). Putative transformants are identified by their faster growth on the selective medium relative to nontransformed tissue. Screenable markers (e.g., green fluorescent protein and β-glucuronidase) can also be used to identify transformed tissue.

As used herein, "plant culture medium" refers to any medium used in the art for supporting viability and growth of a plant cell or tissue, or for growth of whole plant specimens. Such media commonly include defined components including, but not limited to: macronutrient compounds providing nutritional sources of nitrogen, phosphorus, potassium, sulfur, calcium, magnesium, and iron; micronutrients, such as, for example, boron, molybdenum, manganese, cobalt, zinc, copper, chlorine, and iodine; carbohydrates, such as, for example, sucrose glucose, fructose, maltose, galactose, raffinose, stachyose, mannitol and sorbitol; (although maltose may be preferable to sucrose for some media) vitamins; phytohormones; selection agents (for transformed cells or tissues, e.g., antibiotics or herbicides); and gelling agents (e.g., agar, Bactoagar, agarose, Phytagel, Gelrite, etc.); and may include undefined components, including, but not limited to: coconut milk, casein hydrolysate, yeast extract, and activated charcoal. The medium may be either solid or liquid, although solid medium is preferred.

Any conventional plant culture medium can be used as a basis for the formulation of MPM, RM, maturation medium and germination medium when appropriately supplemented as described herein. In addition to the plant culture media discussed in the Examples below (e.g., MS medium and FHG medium), a number of such basal plant culture media are commercially available from Sigma (St. Louis, Mo.) and other vendors in a dry (powdered) form for reconstitution with water.

c. Regeneration Medium

"Regeneration medium" (RM) promotes differentiation of totipotent plant tissues into shoots, roots, and other organized structures and eventually into plantlets that can be transferred to soil. Auxin levels in regeneration medium are reduced relative to MPM or, preferably, auxins are eliminated. It is also preferable that copper levels are reduced (e.g., to levels common in basal plant culture media such as MS medium). It is preferable to include a cytokinin in RM, as cytokinins have been found to promote regenerability of the transformed tissue. However, regeneration can occur without a cytokinin in the medium. Typically, cytokinin levels in RM are from about 0 mg/L to about 4 mg/L. RM also preferably includes a carbon source, preferably about 20 g/L to about 30 g/L, e.g., either sucrose or maltose (there is no preference for maltose for RM).

Optionally, one may employ a conventional shooting medium to promote shoot regeneration from meristematic structures and/or a conventional rooting medium to promote root formation. For example, MS basal medium supplemented with IBA (e.g., 0.5 mg/L) can be used to induce root formation, if necessary. Root induction is preferred for corn. Depending upon the genotype, different levels of an auxin and cytokinin (i.e., a different auxin/cytokinin ratio) provide optimal results. Conventional shooting and rooting media are considered regeneration media.

Any well-known regeneration medium may be used for the practice of the methods of the present invention.

d. Maturation Medium

Following isolation, immature embryos can be incubated on maturation medium. Maturation medium promotes the maturation of such embryos. Generally, maturation medium comprise a basal plant culture medium, such as, for example, MS or FHG. Preferably, maturation medium further comprises a carbon source, including, but not limited to, sucrose and maltose. While the invention does not depend on a maturation medium having a particular concentration of a carbon source, the concentration is typically about 15% for sucrose. Preferably the sucrose concentration is between about 6% and about 15%. Maturation medium may contain hormones such as ABA, typically in the concentration of about 0.1 μM to about 1.0 μM.

e. Germination Medium

As described herein, germination medium promotes the germination of embryos, whereby a seedling results. Generally, germination medium comprises a basal plant culture medium, such as, for example, MS or FHG. Preferably, germination medium further comprises a carbon source, including, but not limited to, sucrose and maltose. While the invention does not depend on a germination medium having a particular concentration of a carbon source, the concentration is typically about 20 g/L to about 30 g/L for sucrose or maltose.

f. Introduction of Nucleic Acids

A number of methods can be used to introduce nucleic acids into the meristematic cells, including particle bombardment. Particle bombardment has been employed for transformation of a number of plant species, including barley (see, e.g., Wan and Lemaux, 1994, and BioRad Technical Bulletin 2007) and corn (see, e.g., Gordon-Kamm et al., 1990, Wan et al., 1995), for example. Successful transformation by particle bombardment requires that the target cells are actively dividing, accessible to microprojectiles, culturable in vitro, and totipotent, i.e., capable of regeneration to produce mature fertile plants. As described herein, a meristematic tissue (including, but not limited to a vegetative shoot meristem, such as an apical meristem from primary or axillary shoots, young stem tissue, or a young leaf base) is cultured in vitro to cause the formation of adventitious meristematic tissues containing cells that are the target for bombardment. Young et al, U.S. Pat. No. 6,570,068, describe methods of biolistic DNA bombardment transformation protocols applied to different maize tissues and is herein incorporated by reference.

Microprojectile bombardment can be accomplished at normal rupture pressures, e.g., at about 1100 psi, although lower rupture pressures can be used to reduce damage of the target tissue, e.g., about 600 to 900 psi. It has been found that meristematic tissues recover better from the tissue damage caused by bombardment than callus tissue, permitting higher rupture pressures to be used.

In addition to particle bombardment, conventional methods for plant cell transformation may be used, including but not limited to: (1) *Agrobacterium*-mediated transformation, (2) microinjection, (3) polyethylene glycol (PEG) procedures, (4) liposome-mediated DNA uptake, (5) electroporation, and (6) vortexing with silica fibers.

g. Definitions and Explanations of Terms Used

The following definitions and explanations are provided to facilitate understanding of the invention.

Reproductive unit: A reproductive unit of a plant is any totipotent part or tissue of the plant from which one can obtain progeny of the plant, including, for example, seeds, cuttings, tubers, buds, bulbs, somatic embryos, microspores, cultured cells (e.g., callus, meristematic tissue, or suspension cultures), etc.

Isolated: An isolated nucleic acid is one that has been substantially separated or purified away from other nucleic acid sequences in the cell of the organism in which the nucleic acid naturally occurs, i.e., other chromosomal and extrachromosomal DNA and RNA. The term also embraces recombinant nucleic acids and chemically synthesized nucleic acids.

Operably Linked: Nucleic acids can be expressed in plants or plant cells under the control of an operably linked promoter that is capable of driving expression in a cell of a particular plant. A first nucleic-acid sequence is operably linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary, to join two protein coding regions to produce a hybrid protein.

Recombinant: A recombinant nucleic acid is made by an artificial combination of two otherwise separated segments of sequence, e.g., by chemical synthesis or by the manipulation of isolated segments of nucleic acids by conventional genetic engineering techniques.

Transformed; Transgenic: A cell, tissue, organ, or organism into which a foreign nucleic acid, such as a recombinant vector, has been introduced is considered "transformed" or "transgenic," as is progeny thereof in which the foreign nucleic acid is present. This foreign nucleic acid can be from the plant itself. A transformed tissue or plant may include some cells that are not transformed, i.e., may be chimeric, comprising transformed and untransformed cells. Such chimeric tissues may be used to regenerate transformed plants, and may be advantageous for this purpose since less in vitro propagation and selection will be required to produce chimeric tissues than tissues in which 100% of the cells are transformed. Regeneration of chimaeric tissues will generally give rise to chimaeric plants, i.e., plants comprised of transformed and non-transformed cells. Reproduction of these chimaeric plants by asexual or sexual means may be employed to obtain plants entirely comprised of transformed cells.

"Foreign" nucleic acids are nucleic acids that would not normally be present in the host cell, particularly nucleic acids that have been modified by recombinant DNA techniques. The term "foreign" nucleic acids also includes host genes that are placed under the control of a new promoter or terminator sequence, for example, by conventional techniques. This new promoter or terminator sequence can also be from the host plant itself.

Vectors, Transformation, Host cells: Nucleic acids can be incorporated into recombinant nucleic-acid constructs, typically DNA constructs, capable of being introduced into and replicating in a host cell. Such a construct preferably is a vector that includes sequences that are capable of transcription and translation of a polypeptide in a given host cell (and may include a replication system, although direct DNA introduction methods conventionally used for monocot transformation do not require this).

For the practice of the present invention, conventional compositions and methods for preparing and using vectors and host cells are employed, as discussed, inter alia, in Sambrook et al., 1989, or Ausubel et al, 1992.

A number of vectors suitable for stable transformation of plant cells or for the establishment of transgenic plants have been described in, e.g., Pouwels et al., 1987, Weissbach and Weissbach, 1989, and Gelvin et al., 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters useful for expressing genes in plant cells include, but are not limited to, the cauliflower mosaic virus (CaMV) 35S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters), light (e.g., pea rbcS-3A or maize rbcS promoters or chlorophyll a/b-binding protein promoter); phytohormones, such as abscisic acid; wounding (e.g., wunl); anaerobiosis (e.g., Adh); and chemicals such as methyl jasminate, salicylic acid, or safeners. It may also be advantageous to employ well-known organ-specific promoters such as endosperm-, embryo-, root-, phloem-, or trichome-specific promoters, for example.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

Screenable markers are also used for plant cell transformation, including color markers such as genes encoding β-glucuronidase (gus) or anthocyanin production, or fluorescent markers such as genes encoding luciferase or green fluorescence protein (GFP).

The invention is illustrated by the following Example.

EXAMPLE

Transformation of Maize Elite Inbreds Using In Vitro Shoot Meristematic Cultures Induced from Stem Tissue The transformation of model cultivars of maize has been reported (for review, Gordon-Kamm, 1999). The reported methods involve the transformation of immature embryos (IEs) or IE-derived embryogenic callus by particle bombardment, or *Agrobacterium*-mediated delivery, or the transformation of protoplasts by polyethylene glycol or electroporation. However, it remains difficult to use routinely any of these target tissues to obtain fertile transgenic plants from the elite, commercially important, maize inbred lines (Gordon-Kamm, 1999).

Recently, two new target tissues, shoot apical meristems, (SAMs) in IEs (Lowe et al., 1995; 1997) and in vitro-multiplied shoot tips (Zhong et al., 1996), were used to produce transgenic maize. Direct bombardment of the SAMs in IEs was employed to produce stable transgenic sectors in $T_0$ plants in elite inbreds of maize. This approach was limited, however, in utility because of the low efficiency of transgene transmission from the transgenic sectors to progeny. By employing in vitro multiplication of the shoot apices after bombardment, the efficiency of transgene transmission to progeny was improved. However, the application of the improved approach was limited to maize genotypes that respond well to the in vitro shoot multiplication protocol (Lowe et al., 1995).

In vitro-multiplied shoot tips have also been used as target tissues for the transformation of maize. However, a similar limitation as described above was encountered. The transformable genotypes were limited to those that are highly responsive during in vitro shoot multiplication. Stable transformation using this approach has only been reported for two varieties of sweet corn (Zhong et al., 1996). That this is the case is probably due to the fact that the in vitro multiple shoot response from maize inbreds could not be as efficiently induced and/or maintained using the described procedures as that from the sweet corn varieties (Zhong et al. 1992, 1996; Lowe et al., 1995).

Two new transformation methods using in vitro induction of shoot meristematic cultures (SMCs), the Sector Proliferation Method (SPM), and direct SMC induction, are described below. Each of the new methods disclosed herein is an improvement over existing transformation methods for maize, and particularly for commercially important elite maize inbreds.

Materials and Methods

SMC induction. Dry seeds of publicly available maize inbreds (B73, Ohio 43, and Missouri 17) and elite Pioneer Hi-Bred inbreds (PHJ90, PHR81, PHP02, PHN46, and PHP38) were obtained from Pioneer Hi-Bred. Immature ears of elite Pioneer Hi-Bred inbreds (PHTE4 and PHJ90) were harvested from field-grown plants in the winter nursery of Pioneer Hi-Bred in Puerto Rico. In order to provide aseptically germinated seedlings, both dry seeds and immature ears were surface-sterilized with 70% ETOH for 3-5 min and 20% v/v Clorox bleach (5.25% sodium hypochlorite) for 20-25 min, rinsed 3× with sterile water. The sterilized dry seeds were then germinated on germination medium. (GM). Following sterilization, immature embryos were dissected from immature ears and the immature embryos were placed on maturation medium, then on germination medium to germinate. Vegetative shoot segments, including the shoot apical meristem and stem tissues, were isolated from 7-10 day old germinated seedlings, cultured on Meristem Proliferation Medium (MPM) induction medium as previously described (Zhang et al., 1998). Similar methods were used in culturing on various other MPMs including MPM, MPM-MC, MPM-ZN and MPM-MCZN Tissue sectioning and expression analysis of kn1. Plant tissues were fixed in fresh FAA (50% v/v ethanol, 5% v/v glacial acetic acid, 10% v/v formaldehyde (37%), 35% v/v water) for 2 hr at 4° C. and embedded in wax using a microwave protocol (Schichnes et al., 1999). In situ hybridization and immunolocalization techniques followed previously described procedures (Jackson et al, 1994, Zhang et al., 1998).

DNA constructs. Three DNA constructs (see FIG. 1) were used in transformation experiments. The first was p11593 containing a modified streptomycin-resistance gene (aadAm), driven by Ubi1ZM and terminated with PinII. The second, p8092K, contained a maize-optimized PAT gene (moPA7) driven by Ubi1ZM promoter and terminated with CaMV35S termination sequence, and the third, pAGR73, contained uidA driven by the rice Act15' and terminated with rbcS3'.

Production of transgenic $T_0$ plants. For the shoot proliferation method, IEs at the early-coleoptilar stage were isolated from surface-sterilized immature ears of inbreds, PHTE4 and PHJ90, and placed on maturation medium (MS+15% sucrose) for 2-4 hrs, bombarded with p11593 and p8092 (1 μg DNA/bombardment, 1 μm gold particles, and 650 psi). The bombarded IEs were maintained on maturation medium for 1-2 weeks and then transferred to germination medium (MS+2% sucrose) for 1-2 weeks. The germinated seedlings were transferred to streptomycin-containing medium (MS+2% sucrose+50-100 mg/L streptomycin) to screen for plants with green leaf sectors. The shoots with green leaf sectors were excised and transferred to SMC induction medium (without streptomycin). After 1-2 months, the induced SMCs were transferred to shoot regeneration medium (MPM-MC without 0.5 mg/L 2,4-D) to induce shoot regeneration. All regenerated shoots were transferred to rooting medium containing streptomycin (MS+2% sucrose+0.5 mg/L IBA+50-100 mg/L streptomycin). After 1-2 months on rooting medium, the putative transgenic $T_0$ plants, which had full green leaves, were transferred to soil for further growth in the greenhouse and subsequent molecular analysis.

For the transformation of SMCs, shoot segments were cut from germinated seedlings and cultured on modified MPM, as previously described (Zhang et al., 1998). After 4-6 weeks, the induced SMCs from the cultured stem tissues were identified, isolated and bombarded with p8092 and pAGR73. After 3-4 days, the bombarded SMCs were transferred to selection medium containing 3-4 mg/L bialaphos. After 4-5 months on selection medium, herbicide-resistant SMCs were identified and transferred to shoot development medium and then rooting medium, both containing 4 mg/L bialaphos. Putative transgenic $T_0$ plants were transferred to soil in the greenhouse.

DNA hybridization analysis of transgenic plants. Genomic DNA samples were isolated from leaf tissues of putative transgenic plants as described (Cone, 1989), and digested with EcoRI. It has an unique restriction site in p8092K, which releases a 1.8 kb fragment containing aadA from p11593, and a 2.8 kb fragment containing uidA from pAGR73. After digestion, DNA samples were separated by electrophoresis on a 1% agarose gel, transferred to Zeta-Probe GT blotting membrane (Bio-Rad Laboratories, Hercules, Calif.) using downward alkaline blotting (Koctsier et al., 1998), and hybridized, following manufacturer's instructions (Instruction Manual, Zeta-Probe GT Blotting Membranes). $^{32}$P-labeled probes were made from a 0.7 kb PCR product (primers, 5'-AGCGAGGTGGTGGGCGTGAT-3' (SEQ ID NO: 1), 5'-AGTCGGCGGCCACGTCCTT-3' (SEQ ID NO: 2)) containing the aadA coding region of p11593, from a 0.6 kb BamHI-digested fragment containing the moPAT coding region, and from a 1.8 kb PCR product (primers: 5'-TTACGTCCTGTAGAAACC-3' (SEQ ID NO: 3), 5'-TCATTGTTTGCCTCCCGT-3' (SEQ ID NO: 4)) containing the uidA coding region, respectively. After hybridization and washing, blots were, exposed to Kodak Biomax MS film (Fisher Scientific, IL). PCR analysis of transgenic tissues was performed using the following primers moPAT (5'-CGCCTACATACCTCGCTCTG-3' (SEQ ID NO: 5), 5'-CACTGCCCGCTTTCCA-3' (SEQ ID NO: 6)), uidA (as above), and aadA (as above).

Transgene expression analysis of $T_0$, $T_1$ and $T_2$ plants. For phenotypic, analysis of GUS transgene expression, young root or leaf tissues of $T_0$ plants were stained with X-glucuronide at 37° C. for 24 hrs (Jefferson et al., 1987). In order to test for functional expression of moPAT or aadA, regenerated plants were transferred to MS basal medium, containing either 4 mg/L bialaphos or 100 mg/L streptomycin, respectively. Mature $T_1$ and $T_2$ seeds were harvested from each $T_0$ and/or $T_1$ plant grown in the greenhouse, surface-sterilized as described, and germinated on MS basal medium. Phenotypic analysis of transgene expression was conducted on each germinated seedling as described. Segregation ratios of transgene expression in progeny were analyzed using the Chi-square analysis method.

Results

Induction of SMCs from elite maize inbreds. Vegetative shoot segments (1.0-1.5 cm in length) were isolated from IEs or germinated seedlings originating from dry seed, and cultured on MPM induction medium. After 4-6 weeks on MPM, induction frequencies of SMCs were determined from the different inbreds tested. SMCs were induced from 60% to 80% of the cultured shoots of Ohio 43, PHTE4 and PHP38, 30-40% of B73 and PHN46, 10-20% of Missouri 17, PHP02, PHR81 and PHJ90. For each inbred, the induced SMCs were continuously subcultured on MPM. After 4-6 weeks, the SMCs induced from inbreds Ohio 43, PHTE4 and PHP38 proliferated continuously and produced new SMCs; however, the SMCs from the other inbreds, B73, PHN46, Missouri 17, PHP02, PHR81, PHJ90, proliferated very slowly on MPM and eventually died.

Figure 2:
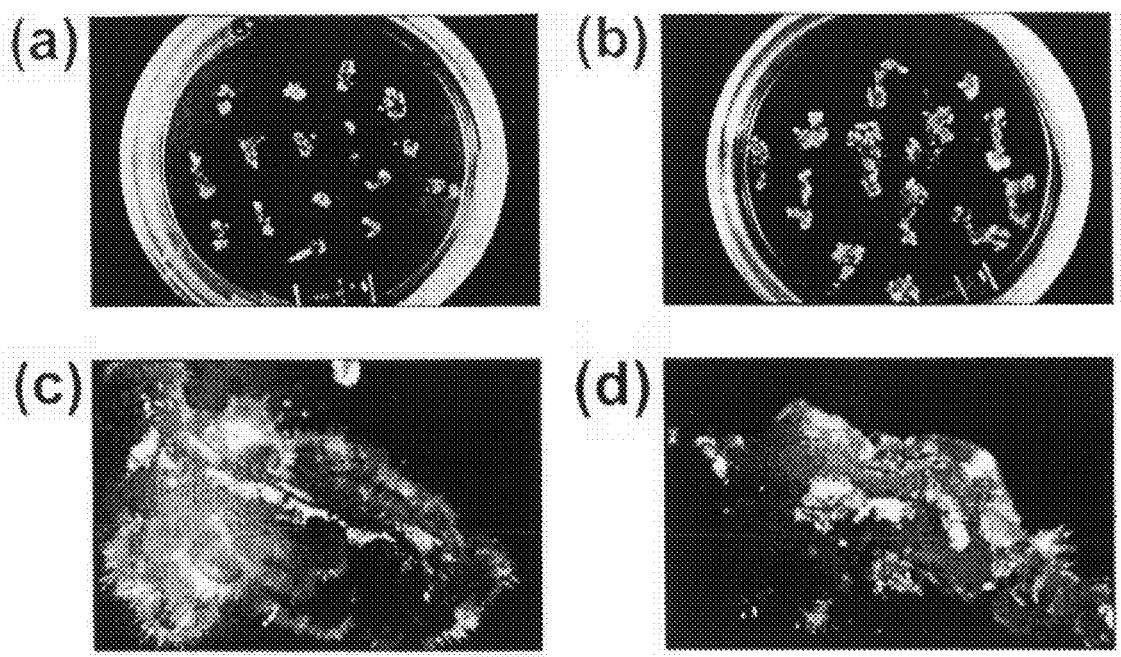
FIG. 2A-D shows SMC induction from inbred B73 on three media. (A) Four-week old cultures on MPM. (B) Four-week old cultures on MPM-MC. (C) a close-up of SMCs induced on MPM-MC. (D) a close-up of SMCs induced on MPM-Zn.

Previous research with barley showed that MPM-MC medium, containing fifty-fold higher levels of copper than MS-basal medium and maltose instead of sucrose, significantly improved the induction and maintenance of SMCs from certain commercial cultivars (Zhang et al., 1999). MPM-MC was thus tested for its effect on induction and maintenance of SMCs from the maize inbreds listed in the above paragraph. After 4-6 weeks of culture on MPM-MC, different genotypes exhibited different SMC induction responses. The inbreds, Ohio 43, PHTE4 and PHP38, which had the highest induction frequencies of all cultivars on MPM medium, had even higher induction frequencies on MPM-MC (80-90%); B73 showed significantly improved induction frequencies, 85-90% on MPM-MC compared to 30-40% on MPM (FIG. 2). Little improvement was observed with the inbreds PHJ90, PHR81, PHP02, PHN46 and Missouri 17.

Figure 3:
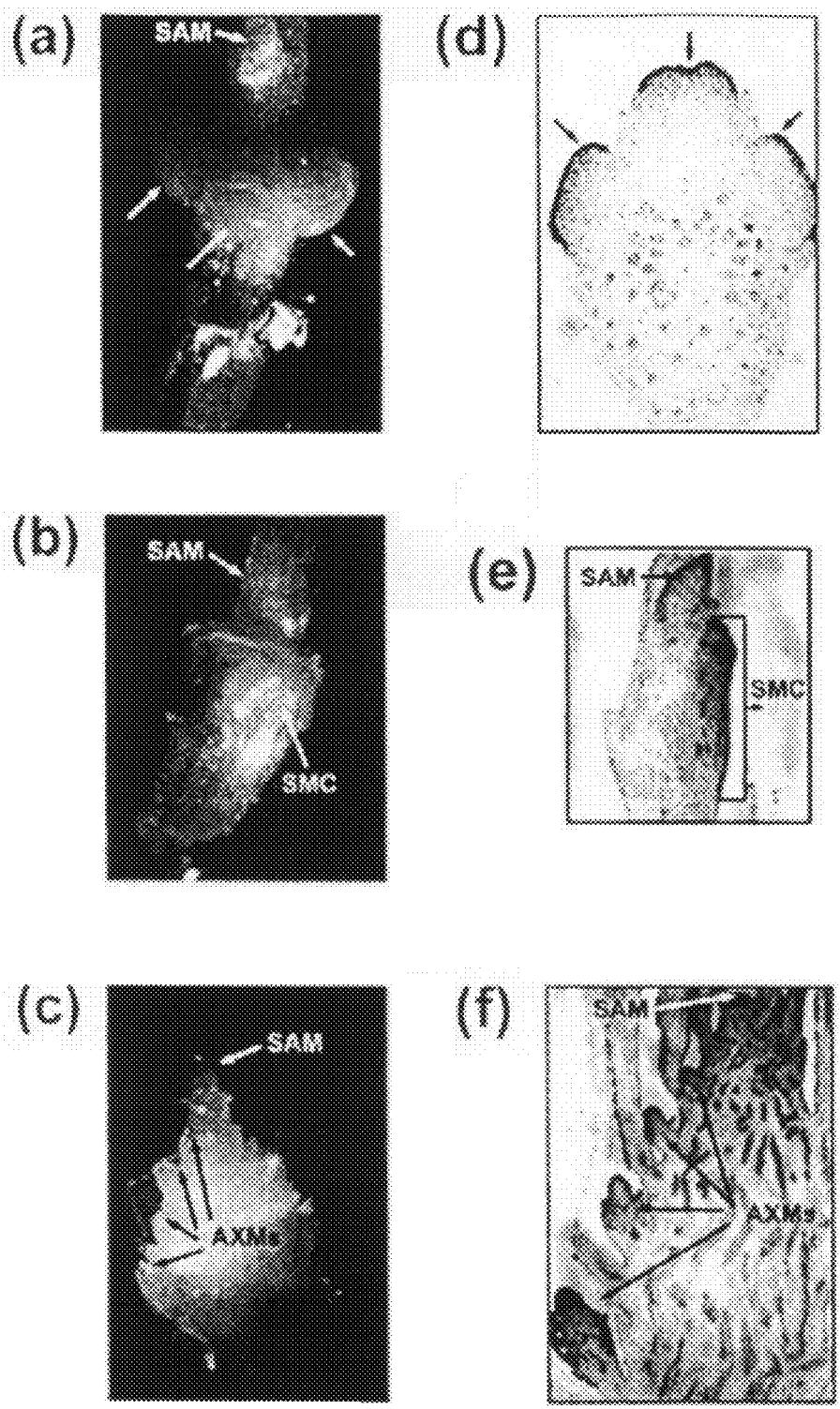
FIG. 3A-F shows cellular and molecular analysis of SMC induction from inbred B73. (A) Shoots cultured for 21 days on MPM-ZN showing SMC induction (arrows) around the stem region below the shoot apical meristem (SAM). (B) 15 day-old cultured shoots on MPM-Zn. (C) Axillary shoot meristem (AXM) proliferation after culture on shoot multiplication medium for 15 days. (D-F) Immunolocalization with anti-KN1 antibody. (D) Cross-section of stem tissue after 21 days of culture on MPM-Zn. (E) Longitudinal section of shoots after 15 days cultured on MPM-Zn. (F) Longitudinal section of shoots after 15 days culture on shoot multiplication medium showing AXM proliferation (arrows).

A new medium was devised to attempt to achieve additional improvements in the responses of the inbreds. This medium contained ten-fold higher levels of $ZnSO_4$ than standard MS-based medium in either MPM (termed MPM-Zn) or MPM-MC (termed MPM-MCZn) media; these media were used in tests of SMC induction of the maize inbreds. On MPM-Zn, inbred B73 showed even higher induction frequencies (90-100%) than on MPM-MC, (85-90%) and also the induced SMCs had fewer differentiated leaves, compared to those induced on MPM-MC (FIG. 3). The SMCs of inbred PHP38 induced on MPM-Zn also showed less leaf differentiation. On MPM-MCZn, no better results were obtained from inbred B73 and PHP38 than on MPM-Zn. All other inbreds examined (Missouri 17, PHN46, G12, PHR81, G71) showed no improvement in SMC induction on either MPM-Zn or MPM-MCZn compared to SMC induction on MPM-MC.

Maintenance of the induced SMCs was tested on MPM-MC or, for B73 and PHP38, MPM-Zn. After 4-6 weeks on MPM-MC, the induced SMCs of B73, PHP38, PHTE4 and Ohio 43 proliferated continuously, producing new SMCs. The SMC cultures of these genotypes were maintained on MPM-MC for more than 12 months without losing the ability to form shoots. On MPM-Zn, the induced SMCs of B73 and PHP38 did not proliferate as vigorously as on MPM-MC. Therefore, for induction of SMCs of PHTE4, PHP38, and Ohio 43, MPM-MC or MPM is optimal; induction of SMCs of B73 is optimal on MPM-Zn. For maintenance of the induced SMCs, however, MPM-MC is the optimal medium for all inbreds tested.

Figure 4:
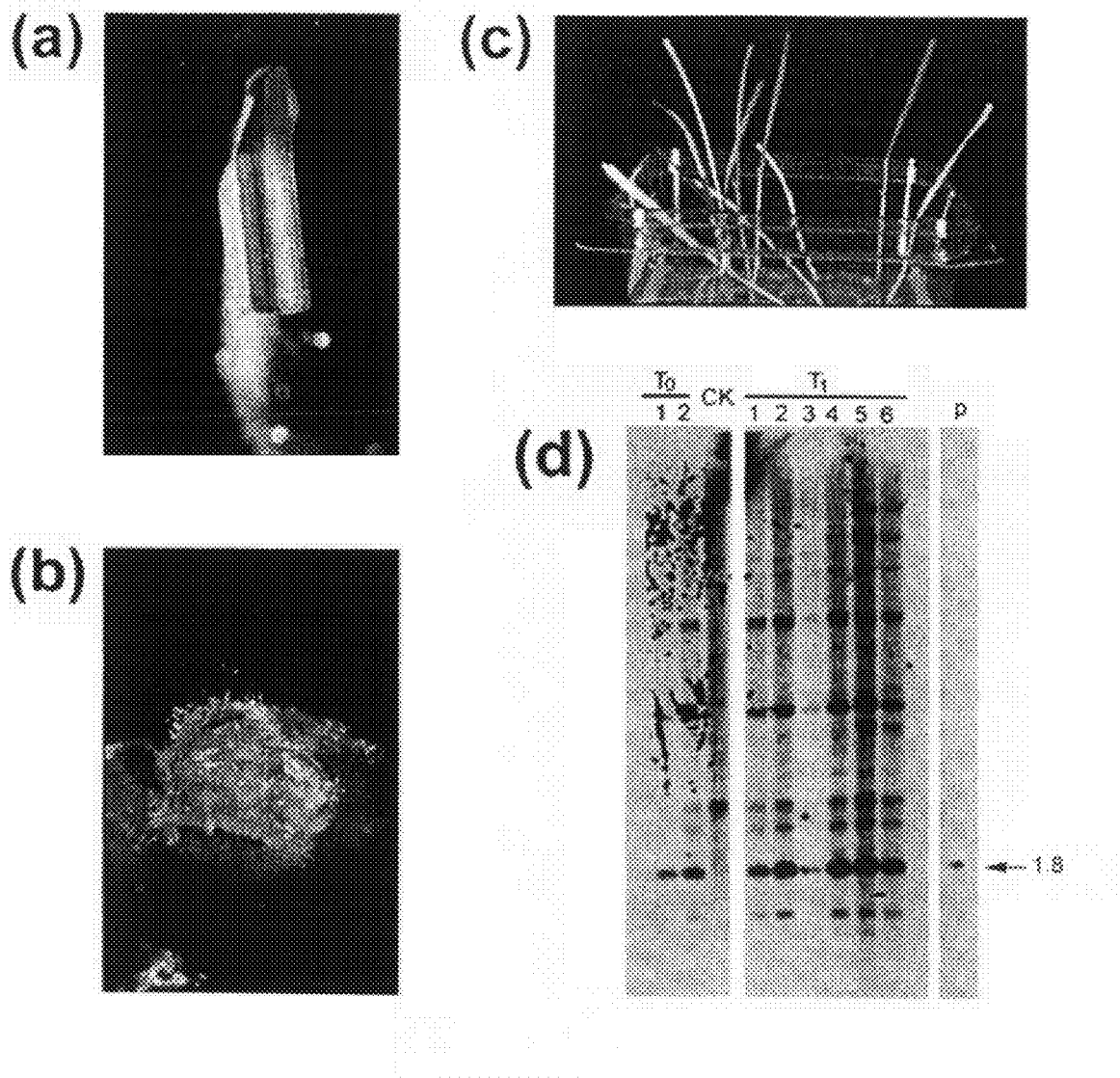
FIG. 4A-D shows transformation of maize inbred PHTE4 using SPM method. (A) A germinated seedling with a green leaf sector on MS basal medium containing 100 mg/L streptomycin. (B) Induced SMCs from the shoot in A after 21 days culture on MPM-MC. (C) Segregation of aadaM expression in $T_1$ progeny. (D) DNA hybridization analysis of DNA from transgenic $T_0$ and $T_1$ plants digested with EcoRI and using an aadaM probe. Lane on right (p) contains p11593 digested with EcoRI. CK=control nontransformed DNA. Molecular weight indicated on right.

Cellular and molecular characterization of SMC induction. After 2-4 weeks on SMC induction medium, the stems of the cultured shoots of the maize inbreds tested were normally elongated; and two to three internodes were easily identified on the elongating stems below the SAMs. In determining the genesis of SMC tissues in B73, most were induced from the two youngest nodal regions in the stem tissues (FIG. 4A) and PHTE4 (FIG. 4B). This type of SMC induction is different from that seen from axillary meristem (AXM) proliferation (FIG. 4C) when isolated shoots were cultured on shoot multiplication medium (CSM) as described (Zhong et al., 1992).

In order to understand SMC induction at the cellular and molecular levels, cultured shoots of inbreds B73 and PHTE4 from different culturing periods were embedded and both cross-sectioned and longitudinally sectioned. Expression of the developmentally regulated maize gene, kn1, was shown to be a reliable marker in maize to identify in vitro shoot meristematic cell proliferation and new shoot meristem formation (Zhang et al., 1998). Immunolocalizations with anti-KN1 antibody or in situ hybridizations with antisense kn1 were used to characterize SMC induction in inbreds B73 and PHTE4. The analysis of the cross-sections of B73 shoots cultured for 21 days showed that SMCs were induced directly from stem tissues (FIG. 4D). In the longitudinally sectioned shoots of B73 cultured for 15 days, analysis of results showed that SMCs were also induced directly from younger stem tissues below the SAM (FIG. 4E), which is different from the situation with AXM proliferation (FIG. 4F). Analysis of longitudinally sectioned twenty-one day-old cultured shoots of PHTE4 showed similar results in that the SMCs appeared to be induced from the KN1-expressing stem tissues below the SAM (data not shown).

Figure 5:
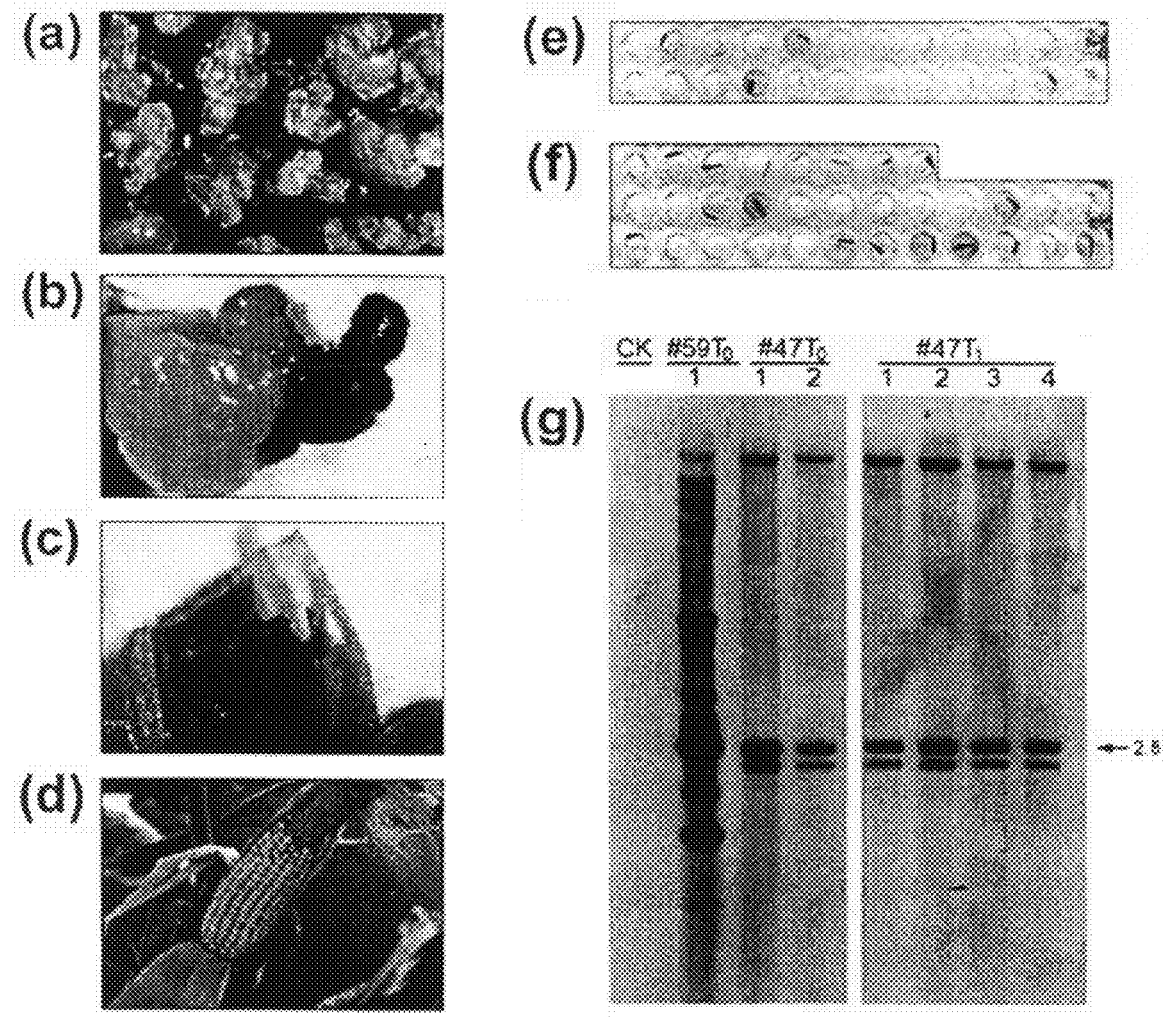
FIG. 5A-G shows transformation of maize inbred B73 using SMCs as target tissues. (A) Isolated SMCs from stem tissues. (B) Chimeric GUS-expressing sectors from herbicide-resistant SMCs after 3-4 months on selection medium containing 4 mg/L bialaphos. (C) Fully transgenic $T_0$ shoots with GUS expression in the shoot apical meristem. (D) A fertile ear after pollination with transgenic pollen on a non-transgenic B73 plant. Segregation of GUS expression in $T_1$ progeny derived from utilizing as the donor transgenic pollen (E) or transgenic ears (F). (G) Hybridization analysis of DNA from one individual $T_0$ from exp. #59, from two individual $T_0$ plants and four individual $T_1$ plants from exp. #47 using a uidA probe. CK=control nontransformed DNA. Molecular weight indicated on right.

Shoot Proliferation Method; Transgenic plants obtained from in vitro proliferation of transgenic sectors. Thousands of coleoptilar stage IEs of maize inbreds, PHTE4 and PHJ90, were isolated and cultured on MS with 15% sucrose for 2-4 hrs, and then bombarded with the constructs, p11593 and p8092K. After 7-15 days, bombarded IEs were transferred to MS medium with 2% sucrose, and after a further 7-10 days, the germinated seedlings were transferred to screening medium (MS medium supplemented with 100 mg/L streptomycin). After approximately two to three months, a total of five plants with green leaf sectors were identified from the bombarded IEs of PHTE4 (FIG. 5A). It was observed in previous experiments that the plants with green leaf sectors usually had transgenic sectors in their stem tissues (Gordon-Kamm et al., 1999). Shoot segments from the five plants were therefore isolated and cultured on MPM-MC medium to induce SMCs. After 1-2 months, SMCs were induced from the stem tissues of two out of the five plants, and the induced SMCs were transferred to shoot regeneration medium to produce shoots (FIG. 5B). Four to six weeks later, approximately 120 shoots were regenerated from the induced SMCs of each of the original two plants. The regenerated shoots were then transferred to MS medium containing 50 mg/L streptomycin to screen for transgenic $T_0$ plants. After six weeks on streptomycin-containing medium, all regenerated shoots deriving from one of the original two plants were white in color. However, from the second original plant, seven regenerated shoots were still fully green. Those seven green shoots were further screened on MS medium containing 100 mg/L streptomycin and after two weeks, the seven putative transgenic $T_0$ shoots were still green on the higher level of streptomycin. All seven putative transgenic $T_0$ shoots were analyzed by PCR using aadA primers; all seven gave positive PCR signals for the presence of aadA in DNA isolated from the shoots. Four of the transgenic $T_0$ shoots produced roots and were transferred to soil for further growth in the greenhouse; the other three transformed $T_0$ shoots remained in culture, but no roots developed.

After 3-4 months growth in the greenhouse, the four transgenic $T_0$ plants matured, produced pollen and ears, and were out-crossed to non-transgenic B73 plants, using either pollen or ears from the transgenic donors. Segregation of expression of aadA in $T_1$ progeny was tested by transferring germinated $T_1$ seedlings to 100 mg/L streptomycin-containing MS medium; segregation analyses gave a ratio of 1:1. Transgenic $T_1$ plants were self-pollinated, and segregation analysis of aadA expression in the $T_2$ progeny yielded a 3:1 ratio (FIG. 5C). DNA hybridization analysis of genomic DNA samples from $T_0$ and $T_1$ plants confirmed the stable integration of the transgene (aadA) in the maize PHTE4 genome (FIG. 5D).

Transgenic plants produced from bombardment of SMCs. Shoot segments of inbred B73 were isolated from germinated seedlings, which originated from dry seeds, and then were cultured on MPM-Zn. After 4-6 weeks, SMCs were induced from the stem tissues of the cultured shoots. The induced SMCs were isolated from the stem tissues and bombarded with constructs of p8092K (UbilZM/moPA7) and pAGR73 (Actl/uidA) (FIG. 6A). Three to four days after bombardment, the SMCs were transferred to MPM-MC selection medium containing 3-4 mg/L bialaphos, and after 3-4 months on selection, seven independent sets of resistant SMC tissue were identified from three independent bombardment experiments (experiment nos. 46, 47, 59). Small pieces of tissue from each putative transgenic SMC were tested for GUS expression. All showed chimeric GUS-expressing sectors (FIG. 6B). The chimeric, putatively transgenic SMCs were continuously cut into small pieces, selected on MPM-MC with 4 mg/L bialaphos, and tested for GUS expression. After 24 weeks, uniformly expressing GUS tissues were obtained from experiment nos. 47 and 59. Transgenic SMCs from experiment no. 46 were lost during the culturing process due to mishandling. The transgenic SMCs from experiment nos. 47 and 59 were then transferred to regeneration medium (MPM-MC with no 2,4-D) containing 4 mg/L bialaphos. Ten to fifty putative transgenic $T_0$ shoots were obtained from each set of resistant SMC tissue and transferred to MS basal medium containing 4 mg/L bialaphos for further selection and rooting. Seven transgenic shoots from experiment no. 47 developed roots (FIG. 6C) and were transferred to soil in the greenhouse. Transgenic $T_0$ shoots obtained from the other resistant SMCs stopped growing at the 3-4 leaf stage; even the shoots that had a few roots did not develop. Genomic DNA was isolated from the transgenic $T_0$ shoots or plants derived from experiment nos. 47 and 59 and DNA hybridization analysis showed that the moPAT and uidA genes were stably integrated in the transgenic $T_0$ plants and each event had a different integration pattern (FIG. 6D).

The seven $T_0$ plants derived from experiment no. 47 matured in the greenhouse after three months and produced fertile pollen and ears, which were cross-pollinated with non-transgenic B73 plants using both transgenic pollen and transgenic ears. Segregation of transgene expression (GUS or herbicide resistance) in $T_1$ progeny was 1:1 when transgenic ears were used with nontransgenic pollen (FIG. 6E); however, lower ratios were observed when transgenic pollen was used with nontransgenic ears. DNA hybridization analyses of $T_1$ plants showed the same integration pattern as that seen in $T_0$ plants (see FIG. 6B).

Discussion

In this example we describe new methods for stable transformation of elite inbreeds of maize, utilizing a Pioneer Hi-Bred inbred, PHTE4, and a publicly held inbred, B73. These described methods are different from previously published transformation protocols in maize (reviewed by Gordon-Kamm., 1999). First, the methods are based on a new type of in vitro culture, shoot meristematic cultures (SMCs). These cultures are composed of KN1-expressing shoot meristematic cells and have the potential to produce in vitro adventitious shoot meristems (ADMs) (Zhang et al., 1998, 1999). As demonstrated herein and elsewhere using histological and molecular analyses (Zhang et al, 1998, 1999), SMCs are morphologically and physiologically different from the shoot apical meristem (SAM) in the IE (Lowe et al, 1995, 1997) and in vitro multiple shoot-tips (Zhong et al., 1992).

Secondly, SMCs are induced primarily from immature stem tissues of the in vitro-cultured vegetative shoots. From cellular and molecular analyses, it was shown that SMCs from the maize elite inbreds were induced from elongating stem tissues in the cultured shoots. The induced SMCs are composed of adventitious shoot meristematic cells, which are characterized by the expression of the developmentally regulated gene maize kn1 (Vollbrecht et al., 1991), and have the potential to produce adventitious shoot meristems (ADMs) as previously described (Zhang et al., 1998). Previously described in vitro-induced cultures in maize were mainly derived from IEs (reviewed by Gordon-Kamm, 1999), SAMs and/or axillary shoots (Zhong et al., 1992; Lowe et al., 1995, 1997), not stem tissues.

The third unique aspect of the described methods is the new media (MPM-MC and MPM-Zn) used for the induction of SMCs. As disclosed herein, for certain elite maize inbreds, like B73, SMCs either could not be efficiently induced as transformation target tissues or the induced SMCs could not be maintained in the absence of using these two media.

The first transformation method disclosed in the present example is an improvement over the previously described method of direct bombardment of the SAM in coleoptilar stage IEs (Lowe et al., 1995, 1997). In that method, the frequency of obtaining transgenic sectors was reasonable, but very few sectors resulted in passage of the transgene to progeny (Lowe et al., 1997). With the implementation of in vitro shoot multiplication after bombardment of the SAMs, the efficiencies of producing transgenic progeny were improved in certain maize inbreds but still very low (Lowe et al., 1995). It is probably due to the fact that transgenic sectors only in the AXMs proliferated, because shoot multiplication was induced only from AXMs and/or SAMs (Zhong et al., 1992; Lowe et al., 1995). In the method described herein, in vitro SMCs are able to be induced from all around the stem tissue. This indicates that a stable transgenic sector in any part of the stem is probably capable of proliferating and giving rise to transgenic plants that pass the transgene on to progeny.

The second transformation method described in this report involves the direct use of SMCs as the target tissue. The induced SMCs have large surface areas and are composed of masses of shoot meristematic cells, each of which is likely to have the potential to produce a new shoot meristem. After bombardment, these shoot meristematic cells can be proliferated and selected for an appropriate period of time when the transgenic plants regenerated from the cultured shoot meristematic cells are entirely composed of transgenic cells and therefore, are able to pass the transgene on to their progeny. The methods of the present invention are different from the previously reported method which involved the use of in vitro shoot-tips as the direct target tissues in the transformation of sweet corn (Zhong et al., 1996). In that method, the shoot meristems in the multiple in vitro shoot-tips were bombarded, and then multiplied by shoot multiplication as in the method previously described for the direct bombardment of SAMs in IEs (Lowe et al., 1995).

In summary, the ability to induce SMCs from stem tissue results in the ability to produce transgenic maize via either the direct use of the cultures as a transformation target or the utilization of the method to increase the efficiency of transformation from SAMs. This capability derives from the fact that it is possible to generate incipient early meristems from the nodes along the stems of inbreds, a capability not previously demonstrated in maize. In addition the SMCs used as direct targets can be generated using materials from dry seeds rather than having to rely on the vagaries of having access to newly pollinated ears from plants grown under optimal conditions.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

REFERENCES

Alberts et al. (1994) *Molecular Biology of the Cell*, 3rd edition, Garland Publishing Inc., New York, pp. 863-910.
Ausubel et al., eds. (1992, with periodic updates) *Current Protocols in Molecular Biology*, Greene Publishing and Wiley-Interscience, New York.
Bajaj (1989) *Biotechnology in Agriculture and Forestry 8: Plant Protoplasts and Genetic Engineering I*, Springer-Verlag, New York.
Barton and Poeting (1993) *Development* 119:823-831.
Becraft et al. (1996) *Science* 273:1406-1409.
Bregitzer et al. (1995) *Plant Cell Tiss. Org. Cult* 43:229-235.
Christensen and Quail (1996) *Transgenic Res.* 5:1-6.
Chiu et al., (1996) *Curr. Biol.* 6:325-330.
Chuck et al. (1996) *Plant Cell* 8:1277-1289.
Colasanti et al. (1991) *Proc. Natl. Acad. Sci. USA* 88:3377-3381.
Colasanti et al. (1993) *Plant Cell* 5:1101-1111.
Cone (1989) Maize Genet Coop. News. Lett. 63:68.
Dahleen (1996) Plant Cell Tiss. Org. Cult. 43:267-269.
Day and Ellis (1985) *Curr. Genet.* 9:671-678.
Devaux et al. (1993) *Mol. Gen. Genet* 241:674-679.
Dunford and Walden (1991) *Curr. Genet* 20:339-347.
Feiler and Jacobs (1990) *Proc. Natl. Acad. Sci. USA* 87:5397-5401.
Ferreira et al. (1991) *Plant Cell* 3:531-540.
Finnie et al. (1989) *Plant Breed.* 103:110-118.
Fobert et al. (1994) *EMBO J.* 13:616-624.
Foroughi-Wehr et al. (1982) *Theor. Appl. Genet.* 62:233-239.
Freeling and Hake (1985) *Genetics* 111:617-634.
Fromm et al. (1986) *Nature* 319:791-793.
Gelinas et al. (1969) *Am. J. Bot* 56:671-678.
Gelvin et al. (1990) *Plant Molecular Biology Manual*, Kluwer Academic Publishers.
Goldenstein and Kronstadt (1986) *Theor. Appl. Genet* 71:631-636.
Gordon-Kamm et al. (1990) *Plant Cell* 2:603.
Gordon-Kamm et al. (1999) Transgenic Cereals-*Zea mays* (maize). In: Vasil, I. K. (ed.), "Molecular Improvement of Cereal Crops," pp 189-253, Kluwer Academic Publisher, Dordrecht, Boston, London.
Hake et al. (1989) *EMBO J.* 8:15-22.
Hang and Bregitzer (1993) *J. Hered.* 84:105-108.
Hareven et al. (1996) *Cell* 84:735-744.
Hemerly et al. (1993) *Plant Cell* 5:1711-1723.
Hirt et al. (1991) *Proc. Natl. Acad. Sci. USA* 88:1636-1640.
Hunter (1988) "Plant regeneration from microspores of barley, *Hordeum vulgare*," PhD thesis, Wye College, University of London, Ashford, England.
Jackson (1991) "In-situ hybridisation in plants," In: Bowles et al., eds., *Molecular Plant Pathology: A Practical Approach*, Oxford University Press, pp. 163-166.
Jackson et al. (1994) *Development* 120:405-413.
Jähne et al. (1991) *Plant Cell. Rep.* 10:1-6.
Jefferson et al. (1987) *EMBO J.* 6:3901-3907.
Kaeppler and Phillips (1993) *In Vitro Cell Dev. Biol.* 29:125-130.
Kao et al. (1991) *Plant Cell Rep.* 9:595-601.
Kasha et al. (1990) "Haploids in cereal improvement: Anther and microspore culture," in: *Gene Manipulation in Plant Improvement II*, ed., Gustafson, Plenum, New York, pp. 213-235.
Koetsier et al. (1993) *Biotechniques* 15:260-262.
Koprek et al. (1996) *Plant Sci* 119:79-91.
Kott and Kasha (1984) *Can. J. Bot* 62:1245-1249.
Larkin and Scowcroft (1981) *Theor. Appl. Genet* 60:197-214.
Laux et al. (1996) *Development* 122:87-96.
Lehman et al. (1996) *Cell* 85:183-194.
Lemaux et al. (1996) *Bombardment-mediated transformation methods for barley*, Bio-Rad US/EG Bulletin 2007:1-6.
Lewin (1994) Genes V, Oxford University Press: New York.
Lincoln et al. (1994) *Plant Cell* 6:1859-1876.
Long et al. (1996) *Nature* 379:66-69.
Lowe et al. (1995) *Bio/Technology* 13:677-682.
Lowe et al. (1997) Transformation of the maize apical meristem: Transgenic sectors reorganization and germline transmission. In: Tsaftaris, A. S. (ed.), "Genetics, Biotechnology and Breeding of Maize and *Sorghum*," pp 94-97, Royal Society of Chemstry, Cambridge.
Lucas et al. (1996) *Science* 270:1980-1983.
Martinez et al. (1992) *Proc. Natl. Acad. Sci. USA* 89:7360-7364.
Matsuoka et al. (1993) *Plant Cell* 5:1039-1048.
Moore (1995) *Curr. Opinion Genet & Dev.* 5:717-724.
Moore et al. (1991) *Genomics* 10:469-476.
Mouritzen and Holm (1994) *J. Plant Physiol.* 144:586-593.
Muller et al. (1995) *Nature* 374:727-730.
Murashige and Skoog (1962) *Physiol. Plant.* 15:473-497.
Pinkel et al., *Proc. Natl. Acad. Sci. USA* 85:9138-9142, 1988.
Potrykus et al. (1977) *Mol. Gen. Genet.* 156:347-350.
Pouwels et al. (1985, supp. 1987) *Cloning Vectors: A Laboratory Manual*.
Rieger et al. (1991) *Glossary of Genetics: Classical and Molecular*, 5th edition, Springer-Verlag: New York.
Salmenkallio-Marttila et al. (1995) *Plant Cell Rep.* 15:301-304.
Sambrook et al., eds. (1989) *Molecular Cloning: A Laboratory Manual*, 2nd ed., Cold Spring Harbor Laboratory Press: Cold, Spring Harbor, N.Y.
Schichnes et al. (1999) *Microsc. Microanal.* 4:491-496.
Shaul et al. (1996) *Crit. Rev. Plant Sci.* 15:97-112.
Sinha et al. (1993) *Genes Dev.* 7:787-795.
Smith et al. (1992) *Development* 116:21-30.

Smith et al. (1995) *Dev. Genet* 16:344-348.
Snow and Snow (1951) *Proc. R. Soc. Lond. Ser. B* 139:545-566.
Somers et al. (1992). Bio/*technology* 10:1589-1594.
Somers et al. (1994) Genetic engineering of oat. In: Henry R J (Ed.) Improvement of Cereal Quality by Genetic Engineering. Plenum Press, New York. pp 37-46.
Souer et al. (1996) *Cell* 85:159-170.
Steeves and Sussex (1989) *Patterns in Plant Development*, 2nd edition, Cambridge University Press: Cambridge.
Sussex (1952) *Nature* 170:755-757.
Thorpe (1994) "Morphogenesis and regeneration," In: Vasil and Thorpe, eds., *Plant Cell and Tissue Culture*, Kluwer Academic Publishers, Dordrecht, pp. 17-36.
Torbert et al. (1995) *Plant Cell Rep.* 14:635-640.
Vain et al. (1993) *Plant Cell Tiss. Org. Cult* 33:237-246.
van de Sande et al. (1996) *Science* 273:370-373.
Vasil and Vasil (1992) *Physiol. Plant* 85:279-283, 1992.
Vollbrecht et al. (1991) *Nature* 350:241-243.
Wan and Lemaux (1994) *Plant Physiol.* 104:37-48.
Wan et al. (1995) *Planta* 196:7-14.
Wan et al. (1994) Plant Physiol. 104:37-48.
Weigel and Nilsson (1995) *Nature* 377:495-500.
Weissbach and Weissbach (1989) *Methods for Plant Molecular Biology*, Academic Press: New York.
Zhang et al (1996) *J. Plant Physiol.* 148:667-671.
Zhang et al. (1998) *Planta* 204:542-549.
Zhang et al. (1999) *Plant Cell Rep.* 18:959-966.
Zhong et al (1992) *Planta* 187:483-489.
Zhong et al. (1996) *Plant Physiol.* 110:1097-1107.
Ziauddin and Kasha (1990) *Euphytica* 48:279-286.

What is claimed is:

1. A method for producing a transformed maize plant comprising;
   (a) inducing a shoot meristem culture by culturing on a meristem proliferation medium an isolated maize tissue selected from the group consisting of vegetative shoot meristem tissue, meristem tissue from axillary shoot, stem tissue, or leaf base tissue;
   (b) introducing a nucleic acid into at least one cell of the shoot meristem culture;
   (c) selecting the transformed cells; and
   (d) growing the transformed cells in a regeneration medium so as to produce a transformed plant,
wherein the meristem proliferation medium comprises from 0 mg/L to about 3 mg/L of an auxin, from about 2 mg/L to about 8 mg/L of a cytokinin, from about 10 g/L to about 60 g/L of maltose or about 10 g/L to about 60 g/L of sucrose; from about 0.1 µM to about 50 µM copper; and greater than about 35 µM zinc.

2. The method of claim 1 where the maize is selected from the group consisting of B73, Ohio 43, Missouri 17, PHJ90, PHR81, PHP02, PHN46, and PHP38, PHTE4 and PHJ90.

3. The method of claim 1 where the maize is B73.

4. The method of claim 1 wherein the shoot meristematic culture is maintained on MPM MC.

5. A method for producing a transformed maize plant that is recalcitrant to transformation comprising;
   (a) inducing a shoot meristem culture by culturing on a meristem proliferation medium an isolated maize stem tissue;
   (b) introducing a nucleic acid into at least one cell of the shoot meristem culture;
   (c) selecting the transformed cells; and
   (d) growing the transformed cells in a regeneration medium so as to produce a transformed plant.

6. The method of claim 1 where the zinc concentration is from about 60 µM to about 1500 µM.

7. The method of claim 1 where the zinc concentration is from about 100 µM to about 500 µM.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
agcgaggtgg tgggcgtgat                                              20

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
agtcggcggc cacgtcctt                                               19

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
ttacgtcctg tagaaacc                                                18

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
tcattgtttg cctcccgt                                                18

<210> SEQ ID NO 5
<211> LENGTH: 20
<212> TYPE: DNA
<213> ORGANISM: Artificial Sequence
<220> FEATURE:
```

```
-continued

<223> OTHER INFORMATION: Primer

<400> SEQUENCE: 5
cgcctacata cctcgctctg                                              20

<210> SEQ ID NO 6
<211> LENGTH: 16
<212> TYPE: DNA
<213> ORGANISM: Artificial Sequence
<220> FEATURE:
<223> OTHER INFORMATION: Primer

<400> SEQUENCE: 6
cactgcccgc tttcca                                                  16
```